(12) United States Patent
Omote et al.

(10) Patent No.: US 10,302,579 B2
(45) Date of Patent: May 28, 2019

(54) GRAZING INCIDENCE X-RAY FLUORESCENCE SPECTROMETER AND GRAZING INCIDENCE X-RAY FLUORESCENCE ANALYZING METHOD

(71) Applicant: RIGAKU CORPORATION, Tokyo (JP)

(72) Inventors: Kazuhiko Omote, Akishima (JP); Takashi Yamada, Takatsuki (JP)

(73) Assignee: Rigaku Corporation, Akishima-shi, Tokyo (JP)

(*) Notice: Subject to any disclaimer, the term of this patent is extended or adjusted under 35 U.S.C. 154(b) by 0 days.

(21) Appl. No.: 15/628,737

(22) Filed: Jun. 21, 2017

(65) Prior Publication Data
US 2017/0284949 A1 Oct. 5, 2017

Related U.S. Application Data

(63) Continuation of application No. PCT/JP2015/078041, filed on Oct. 2, 2015.

(30) Foreign Application Priority Data

Dec. 25, 2014 (JP) .................................. 2014-262464

(51) Int. Cl.
*G01N 23/22* (2018.01)
*G01N 23/223* (2006.01)
(Continued)

(52) U.S. Cl.
CPC ....... *G01N 23/223* (2013.01); *G01N 15/0211* (2013.01); *G01N 23/2055* (2013.01);
(Continued)

(58) Field of Classification Search
CPC ............................. G01N 23/22; G01N 23/223
(Continued)

(56) References Cited

U.S. PATENT DOCUMENTS 4,169,228 A * 9/1979 Briska .................. G01N 23/223
378/45
5,220,591 A * 6/1993 Ohsugi .............. G01N 23/2206
378/44
(Continued)

FOREIGN PATENT DOCUMENTS

CN 101253410 A 8/2008
CN 102930918 A 2/2013
(Continued)

OTHER PUBLICATIONS

International Preliminary Report on Patentability with translation of the Written Opinion issued from the International Bureau in counterpart International Application No. PCT/JP2015/078041, dated Jul. 6, 2017.
(Continued)

*Primary Examiner* — Allen C. Ho
(74) *Attorney, Agent, or Firm* — Sughrue Mion, PLLC

(57) ABSTRACT

A grazing incidence X-ray fluorescence spectrometer (1) of the present invention includes: a bent spectroscopic device (4) to monochromate X-rays (3) from an X-ray source (2) and generate an X-ray beam (5) focused on a fixed position (15) on a surface of a sample (S); a slit member (6) disposed between the bent spectroscopic device (4) and the sample (S) and having a linear opening (61); a slit member moving unit (7) to move the slit member (6) in a direction that intersects the X-ray beam (5) passing through the linear opening (61); a glancing angle setting unit (8) to move the slit member (6) by using the slit member moving unit (7), and set a glancing angle (α) of the X-ray beam (5) to a desired angle; and a detector (10) to measure an intensity of fluorescent X-rays (9) from the sample (S) irradiated with the X-ray beam (5).

7 Claims, 5 Drawing Sheets

(51) Int. Cl.
*G21K 1/02* (2006.01)
*G21K 1/06* (2006.01)
*G21K 1/04* (2006.01)
*G01N 15/02* (2006.01)
*G01N 23/2055* (2018.01)
*G01N 23/207* (2018.01)

(52) U.S. Cl.
CPC ......... *G01N 23/2076* (2013.01); *G01N 23/22* (2013.01); *G21K 1/02* (2013.01); *G21K 1/04* (2013.01); *G21K 1/06* (2013.01); *G21K 1/062* (2013.01)

(58) Field of Classification Search
USPC .......................................... 378/44–46, 48–50
See application file for complete search history.

(56) References Cited

U.S. PATENT DOCUMENTS

| | | | | |
|---|---|---|---|---|
| 5,249,216 | A * | 9/1993 | Ohsugi | G01N 23/2206 378/44 |
| 5,406,609 | A | 4/1995 | Arai et al. | |
| 5,537,451 | A * | 7/1996 | Serebryakov | G01N 23/223 378/44 |
| 5,732,120 | A * | 3/1998 | Shoji | G01N 23/223 378/210 |
| 5,742,658 | A * | 4/1998 | Tiffin | G01N 23/20 257/E21.53 |
| 5,754,620 | A * | 5/1998 | Hossain | G01N 23/223 378/44 |
| 5,841,016 | A * | 11/1998 | Hossain | G01N 23/2251 73/1.01 |
| 5,866,899 | A * | 2/1999 | Hossain | G01N 23/22 250/252.1 |
| 6,041,096 | A * | 3/2000 | Doi | G01N 23/223 378/45 |
| 6,043,486 | A * | 3/2000 | Hossain | G01N 23/22 250/252.1 |
| 6,173,036 | B1 * | 1/2001 | Hossain | G01N 23/223 378/45 |
| 6,317,483 | B1 * | 11/2001 | Chen | B82Y 10/00 378/145 |
| 6,376,267 | B1 * | 4/2002 | Noack | B82Y 15/00 378/70 |
| 6,381,303 | B1 * | 4/2002 | Vu | G01N 23/20 378/46 |
| 6,389,102 | B2 * | 5/2002 | Mazor | G01N 23/20 250/208.1 |
| 6,504,900 | B2 * | 1/2003 | Kondo | G01N 23/20 378/34 |
| 6,577,704 | B1 * | 6/2003 | Holz | G01N 23/2076 378/44 |
| 6,611,577 | B1 * | 8/2003 | Yamagami | G01N 23/223 378/207 |
| 6,628,748 | B2 * | 9/2003 | Michaelsen | B82Y 10/00 252/506 |
| 6,650,728 | B2 * | 11/2003 | Michaelsen | B82Y 10/00 378/49 |
| 6,763,086 | B2 * | 7/2004 | Platonov | B82Y 10/00 378/49 |
| 6,816,570 | B2 * | 11/2004 | Janik | G01N 23/20 378/50 |
| 6,829,327 | B1 * | 12/2004 | Chen | G01N 23/223 378/44 |
| 6,836,533 | B2 * | 12/2004 | Shimizu | B82Y 10/00 378/42 |
| 6,895,071 | B2 * | 5/2005 | Yokhin | G01T 1/36 378/45 |
| 6,934,359 | B2 * | 8/2005 | Chen | B82Y 10/00 378/45 |
| 6,987,832 | B2 * | 1/2006 | Koppel | G01N 23/20 378/50 |
| 7,110,491 | B2 * | 9/2006 | Mazor | G01N 23/20 378/71 |
| 7,113,567 | B2 * | 9/2006 | Michaelsen | B82Y 10/00 378/44 |
| 7,187,751 | B2 * | 3/2007 | Kawahara | G01N 23/223 378/45 |
| 7,358,494 | B1 * | 4/2008 | Gao | G01N 23/227 250/288 |
| 7,406,153 | B2 * | 7/2008 | Berman | G01N 23/20 378/86 |
| 7,415,096 | B2 * | 8/2008 | Sherman | G21K 1/06 378/70 |
| 7,424,092 | B2 * | 9/2008 | Terada | G01N 23/223 378/44 |
| 7,450,685 | B2 * | 11/2008 | Kataoka | G01N 23/223 378/45 |
| 7,471,762 | B2 * | 12/2008 | Ito | G01N 23/223 378/44 |
| 7,483,513 | B2 * | 1/2009 | Mazor | G01N 23/20 378/71 |
| 7,604,406 | B2 | 10/2009 | Tsuji et al. | |
| 7,649,978 | B2 * | 1/2010 | Mazor | G01N 23/201 378/86 |
| 7,680,243 | B2 * | 3/2010 | Yokhin | G01N 23/2206 378/45 |
| 7,899,154 | B2 * | 3/2011 | Chen | G01N 23/223 378/45 |
| 7,991,116 | B2 * | 8/2011 | Chen | B82Y 10/00 250/503.1 |
| 8,243,878 | B2 * | 8/2012 | Yokhin | G01N 23/207 378/70 |
| 8,437,450 | B2 * | 5/2013 | Wall | G01N 23/207 378/73 |
| 8,513,603 | B1 * | 8/2013 | Lederman | G01N 23/223 250/305 |
| 8,565,379 | B2 * | 10/2013 | Mazor | G01N 21/33 378/88 |
| 8,687,766 | B2 * | 4/2014 | Wormington | G01N 23/207 378/70 |
| 8,744,046 | B2 * | 6/2014 | Yamauchi | G01N 23/201 378/70 |
| 8,903,040 | B2 * | 12/2014 | Maeyama | G01N 23/207 378/45 |
| 9,036,789 | B2 * | 5/2015 | Masaki | G21K 1/062 378/149 |
| 9,448,191 | B2 * | 9/2016 | Utaka | G01N 23/2076 |
| 9,551,677 | B2 * | 1/2017 | Mazor | G01N 23/223 |
| 9,594,036 | B2 * | 3/2017 | Yun | G01N 23/223 |
| 9,746,433 | B2 * | 8/2017 | Yamada | G01N 23/223 |
| 2003/0169845 | A1 | 9/2003 | Doi et al. | |
| 2003/0169846 | A1 | 9/2003 | Janik et al. | |
| 2009/0147912 | A1 | 6/2009 | Tsuji et al. | |

FOREIGN PATENT DOCUMENTS

| | | |
|---|---|---|
| CN | 103175857 A | 6/2013 |
| CN | 103323478 A | 9/2013 |
| CN | 103808745 A | 5/2014 |
| JP | 54-007991 A | 1/1979 |
| JP | 3-082943 A | 4/1991 |
| JP | 2001-124711 A | 5/2001 |
| JP | 2003-255089 A | 9/2003 |
| JP | 2008-032703 A | 2/2008 |
| WO | 2007/026750 A1 | 3/2007 |

OTHER PUBLICATIONS

Argument for Japanese Patent Application No. 2016-550291, dated Dec. 21, 2016.
Decision of Grant for Japanese Patent Application No. 2016-550291, dated Feb. 21, 2017.
Notification of Reason(s) for Rejection for Japanese Patent Application No. 2016-550291, dated Nov. 1, 2016.
International Search Report of PCT/JP2015/078041, dated Dec. 22, 2015. [PCT/ISA/210].

(56) References Cited

OTHER PUBLICATIONS

Communication dated Apr. 18, 2018 issued by the State Intellectual Property Office of People's Republic of China in counterpart Chinese Application No. 201580069728.2.
Communication dated Nov. 16, 2018, from the State Intellectual Property Office of People's Republic of China in counterpart Application No. 201580069728.2.
Communication dated Jul. 20, 2018 from the European Patent Office in counterpart Application No. 15872403.9.

* cited by examiner

GRAZING INCIDENCE X-RAY FLUORESCENCE SPECTROMETER AND GRAZING INCIDENCE X-RAY FLUORESCENCE ANALYZING METHOD

CROSS REFERENCE TO THE RELATED APPLICATION

This application is a continuation application, under 35 U.S.C. § 111(a), of international application No. PCT/JP2015/078041, filed Oct. 2, 2015, which claims priority to Japanese patent application No. 2014-262464, filed Dec. 25, 2014, the entire disclosure of which is herein incorporated by reference as a part of this application.

BACKGROUND OF THE INVENTION

Field of the Invention

The present invention relates to a grazing incidence X-ray fluorescence spectrometer and a grazing incidence X-ray fluorescence analyzing method which allows a glancing angle of primary X-rays, from an X-ray source, with which a sample is irradiated, to be automatically adjusted.

Description of Related Art

To date, an X-ray fluorescence spectrometer that includes: a plurality of X-ray sources; an X-ray source selection unit that selects one X-ray source from among the plurality of X-ray sources; an X-ray source adjustment unit that adjusts a position of the X-ray source; and a spectroscopic device position adjustment unit that adjusts a position of a spectroscopic device, such that an intensity of fluorescent X-rays generated from a sample is maximized, and that can perform analysis constantly with high sensitivity and high accuracy in a short time period by automatically adjusting an irradiation position and an irradiation angle of primary X-rays from the X-ray source selected according to a purpose of the analysis, has been known (Patent Document 1).

RELATED DOCUMENT

Patent Document

[Patent Document 1] JP Laid-open Patent Publication No. 2008-32703

SUMMARY OF THE INVENTION

However, the X-ray fluorescence spectrometer needs to be provided with a lot of units such as: the X-ray source selection unit that selects one X-ray source from among the plurality of X-ray sources; the X-ray source adjustment unit that adjusts a position of the X-ray source; and the spectroscopic device position adjustment unit that adjusts a position of the spectroscopic device, and the structure of the spectrometer becomes complicated, which leads to increase of cost.

The present invention is made in view of the problem of the conventional art, and an object of the present invention is to provide a grazing incidence X-ray fluorescence spectrometer that sets, to an optimal angle, a glancing angle that is an angle between a surface of a sample and primary X-rays with which the sample is irradiated, to perform analysis with high sensitivity and high accuracy by using a low-cost simple structure, in various measurement such as quantitative determination of an element in a sample obtained by a solution being dripped and dried on a substrate, and measurement of a film thickness of a thin film sample formed on a substrate.

In order to attain the aforementioned object, a grazing incidence X-ray fluorescence spectrometer according to a first aspect of the present invention includes: an X-ray source configured to emit X-rays; a bent spectroscopic device configured to monochromate the X-rays emitted from the X-ray source and form an X-ray beam that is focused on a fixed position on a surface of a sample; a slit member disposed between the bent spectroscopic device and the sample, the slit member having a linear opening by which a width of the passing X-ray beam is limited in a focusing angle direction; a slit member moving unit configured to move the slit member in a direction that intersects the X-ray beam passing through the linear opening; a glancing angle setting unit configured to move the slit member by using the slit member moving unit, and set a glancing angle of the X-ray beam to a desired angle; and a detector configured to measure an intensity of fluorescent X-rays generated from the sample that is irradiated with the X-ray beam.

The grazing incidence X-ray fluorescence spectrometer according to the first aspect of the present invention sets an optimal glancing angle to perform analysis with high sensitivity and high accuracy by using a low-cost simple structure, in various measurement such as quantitative determination of an element in a sample obtained by a solution being dripped and dried on a substrate, and measurement of a film thickness of a thin film sample formed on a substrate.

In the grazing incidence X-ray fluorescence spectrometer according to the first aspect of the present invention, the slit member is preferably a variable slit member that allows a width of the linear opening to be variable. In this case, the width of the X-ray beam that passes through the slit member can be made variable to change the focusing angle of the X-ray beam according to the purpose of the analysis, thereby performing measurement with enhanced sensitivity and accuracy. In particular, in a case where the width of the linear opening of the variable slit member is widened, the sample is irradiated with the X-ray beam having an enhanced intensity, whereby sensitivity can be further enhanced.

In the grazing incidence X-ray fluorescence spectrometer according to the first aspect of the present invention, the bent spectroscopic device is preferably formed as one of: a multilayer film in which a plurality of layer pairs each including a reflective layer and a spacer layer and each having a predetermined cycle length are layered on a substrate such that a ratio of a thickness of the reflective layer to a thickness of the spacer layer is 1:1.4 to 1:4; and a plurality of multilayer films in each of which a plurality of layer pairs each including a reflective layer and a spacer layer and each having a predetermined cycle length are layered on a substrate, the plurality of multilayer films being formed such that the closer the multilayer film is to the substrate, the less the predetermined cycle length is. This is a first preferable structure.

In a case where the bent spectroscopic device is provided in which the ratio of the thickness of the reflective layer to the thickness of the spacer layer is 1:1.4 to 1:4, not only characteristic X-rays emitted from the X-ray source but also continuous X-rays having ½ of a wavelength as a secondary reflection line, are strongly reflected to simultaneously irradiate the sample therewith. Therefore, analysis can be accurately performed fast over a wide range of wavelength without providing of a plurality of X-ray sources and an X-ray source selection unit that selects one X-ray source from among the plurality of X-ray sources.

In a case where the bent spectroscopic device is provided which has the plurality of multilayer films such that the closer the multilayer film is to the substrate, the less the predetermined cycle length is, X-rays having different energies are reflected by the plurality of multilayer films having the cycle lengths different from each other in the depth direction, and the cycle length is set such that the closer the multilayer film is to the substrate, the less the cycle length is. Therefore, as X-rays have lower energy and are more easily absorbed, the X-rays are reflected at a shallow position closer to the incident surface, and the efficiency of the reflection is high as a whole, and analysis can be accurately performed fast over a wide range of wavelength without providing of a plurality of X-ray sources and an X-ray source selection unit that selects one X-ray source from among the plurality of X-ray sources.

In the first preferable structure described above, it is preferable that a filter configured to be movable forward into and backward from an X-ray optical path from the X-ray source to the sample, the filter having a higher transmittance on a high energy side (short wavelength side), or an applied-voltage variable unit configured to vary a voltage applied to the X-ray source, is further provided, and an intensity ratio among a plurality of X-rays that are included in the X-ray beam and that have different energies is changed by the filter or the applied-voltage variable unit.

In a case where the filter which has the higher transmittance on the high energy side in the X-ray optical path from the X-ray source to the sample, is inserted, reduction of the intensity of the X-rays on the high energy side is not great, and the intensity of the X-rays on the low energy side is reduced, whereby influence of an interfering line on the low energy side can be reduced. In particular, in a case where analyzing of the fluorescent X-rays on the high energy side is performed, signals of the fluorescent X-rays on the low energy side are eliminated, and a so-called dead time of the detector can be shortened.

In a case where the applied-voltage variable unit is provided which can vary the voltage applied to the X-ray source, continuous X-rays generated such that the higher a voltage applied to the X-ray source is, the more intensely the continuous X-rays are generated on the high energy side, are used to change the intensity ratio among the plurality of X-rays that are included in the X-ray beam and have different energies, thereby optimally analyzing an element to be measured can be done.

An X-ray fluorescence analyzing method according to a second aspect of the present invention, performs analysis using the grazing incidence X-ray fluorescence spectrometer according to the first aspect of the present invention.

In the X-ray florescence analyzing method according to the second aspect of the present invention, analysis is performed using the grazing incidence X-ray fluorescence spectrometer according to the first aspect of the present invention. Therefore, the same effect as obtained by the grazing incidence X-ray fluorescence spectrometer according to the first aspect of the present invention can be obtained.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
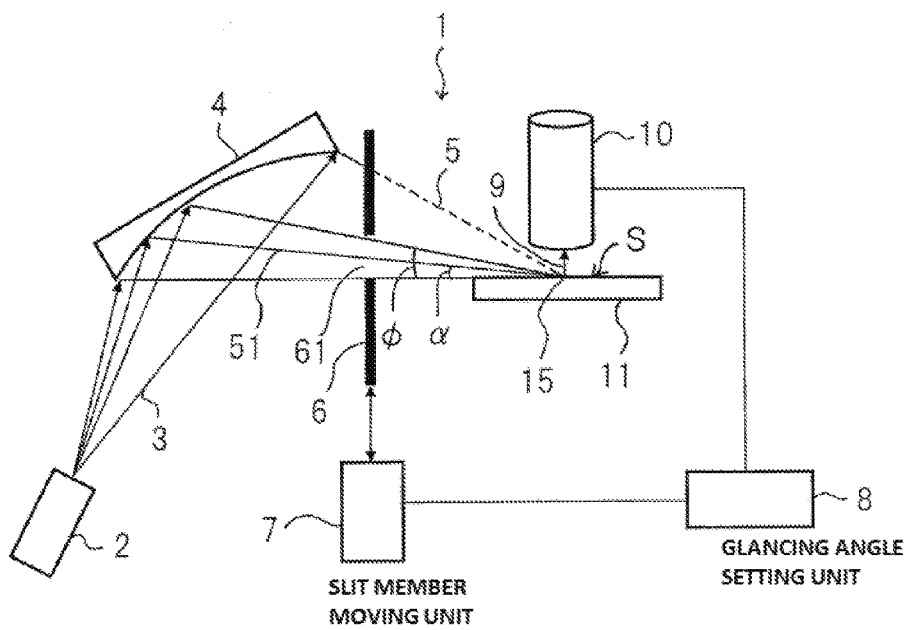
FIG. 1 is a schematic diagram illustrating a grazing incidence X-ray fluorescence spectrometer according to a first embodiment of the present invention.

Hereinafter, a grazing incidence X-ray fluorescence spectrometer according to a first embodiment of the present invention will be described with reference to the drawings. As shown in FIG. 1, the grazing incidence X-ray fluorescence spectrometer 1 includes: an X-ray source 2 that emits X-rays 3; a bent spectroscopic device 4 that monochromates the X-rays 3 emitted from the X-ray source 2, and forms an X-ray beam 5 to be focused on a fixed position on a surface of a sample S; a slit member 6 that is disposed between the bent spectroscopic device 4 and the sample S, and that has a linear opening 61 by which the width of the passing X-ray beam 5 is limited in a focusing angle direction; a slit member moving unit 7 that moves the slit member 6 in a direction that intersects the X-ray beam 5 passing through the linear opening 61; a glancing angle setting unit 8 that moves the slit member 6 by the slit member moving unit 7 to set a glancing angle α of the X-ray beam 5 to a desired angle; and a detector 10 that measures an intensity of fluorescent X-rays 9 generated from the sample S which is irradiated with the X-ray beam 5. The sample S is, for example, a sample substrate 11 on which a sample solution is dripped and dried.

In the grazing incidence X-ray fluorescence spectrometer 1, the X-ray beam 5 with which the sample S is irradiated are incident on a surface of the sample S at a small glancing angle α which is, for example, less than or equal to 0.1° (degree), and most of the X-ray beam 5 is reflected as reflected X-rays and a so-called total reflection phenomenon is caused.

The X-ray source 2 is an X-ray tube having, for example, a molybdenum target. The bent spectroscopic device 4 is, for example, a singly bent spectroscopic device 4, and is produced by a multilayer film being formed on a single crystal substrate which is bent in such a direction that a Mo-Kα line, which forms characteristic X-rays emitted from the X-ray source 2, is reflected to be focused as the X-ray beam 5 in the glancing angle α direction. The single crystal substrate is a silicon substrate, germanium substrate, or the like, and may be doubly bent so as to focus the X-ray beam 5 also in a direction (direction perpendicular to the surface of the drawing sheet) orthogonal to the glancing angle α. The bent spectroscopic device 4 is not limited to the spectroscopic device having the multilayer film formed on the single crystal substrate, and may be formed from a dispersive crystal such as graphite, lithium fluoride, germanium, TAP, or PET and bent by thermoplastic deformation. The detector 10 is, for example, a semiconductor detector such as an SDD or an SSD, and is preferably an SDD that can perform counting at up to a high counting rate.

The slit member 6 has the linear opening 61 having desired length and width. In FIG. 1, the slit member 6 is disposed such that a length direction of the linear opening 61 is parallel with a plane that includes the surface of the sample S. In FIG. 1, the length direction of the linear opening 61 is perpendicular to the surface of the drawing sheet. The X-rays 3 from the X-ray source 2 are incident on the bent spectroscopic device 4 and monochromated, and are focused on the fixed position 15 on the surface of the sample S as the X-ray beam 5 having its width limited by the slit member 6 and having a focusing angle ø limited. The X-ray beam 5 that passes through the linear opening 61 is focused linearly on the fixed position 15 on the surface of the sample S. An angle between the surface of the sample S and X-rays 51 at the center in the focusing angle ø direction in the X-ray beam 5 focused on the sample S, is the glancing angle α.

The slit member 6 is moved, by the slit member moving unit 7, in the direction that intersects the X-ray beam 5 passing through the linear opening 61, for example, is moved in the direction perpendicular to the plane including the surface of the sample S, as indicated by an arrow in FIG. 1. When the slit member 6 is moved upward relative to the surface of the sample S, the glancing angle α is increased. When the slit member 6 is moved downward relative to the surface of the sample S, the glancing angle α is reduced. The glancing angle setting unit 8 measures, by using the detector 10, an intensity of the fluorescent X-rays 9 generated from the sample substrate 11 while moving the slit member 6 by using the slit member moving unit 7, and sets the glancing angle α of the X-ray beam 5 to a desired angle on the basis of the measured intensity of the fluorescent X-rays 9.

Next, an operation of the grazing incidence X-ray fluorescence spectrometer 1 according to the first embodiment will be described. Firstly, in order to set the glancing angle α to a desired angle, the sample substrate 11 that is a silicon wafer is placed on a sample table (not shown) of the grazing incidence X-ray fluorescence spectrometer 1, and measurement of silicon in the sample substrate 11 is started. The sample substrate 11 may be a quartz substrate or a glass substrate.

When the measurement has been started, the X-rays 3 from the X-ray source 2 are incident on the bent spectroscopic device 4, and monochromated and focused as the Mo-Kα line, and the Mo-Kα line passes through the linear opening 61 of the slit member 6 as the X-ray beam 5. The sample substrate 11 is irradiated with the Mo-Kα line that forms the X-ray beam 5 having passed through the linear opening 61 of the slit member 6, and an intensity of a Si-Kα line that forms the fluorescent X-rays 9 generated from the sample substrate 11 is measured by the detector 10 while the slit member 6 is moved upward relative to the surface of the sample substrate 11 by the slit member moving unit 7.

Figure 2:
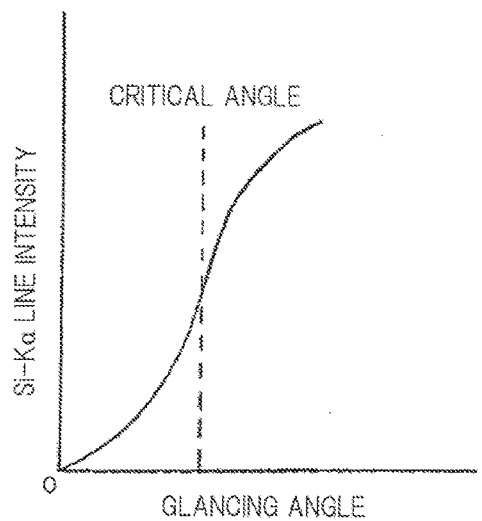
FIG. 2 illustrates a relationship between a glancing angle and an intensity of fluorescent X-rays.

When the slit member 6 is gradually moved upward relative to the surface of the sample substrate 11, the glancing angle α is gradually increased. FIG. 2 shows a relationship between the glancing angle α and the intensity of the fluorescent X-rays 9. The glancing angle setting unit 8 calculates the glancing angle α that maximizes a gradient of change of the intensity of the Si-Kα line in FIG. 2. The calculated glancing angle α is, for example, 0.11°, and the angle that maximizes the gradient of change of the intensity of the Si-Kα line is a critical angle.

The glancing angle setting unit 8 controls the slit member moving unit 7 to move the slit member 6 such that the glancing angle α becomes 0.05° that is about ½ of the calculated critical angle of 0.11°, and sets the glancing angle α to 0.05° that is a desired glancing angle α. The glancing angle may be changed from 0.05° according to the sample S or the condition of the grazing incidence X-ray fluorescence spectrometer 1. When the glancing angle α is less than or equal to the critical angle, the X-ray beam 5 does not enter the sample substrate 11, and the background can be reduced. The glancing angle α that is ½ of the critical angle is an optimal angle for various sample measurement such as quantitative measurement of an element that is dripped and dried on the sample substrate 11, and measurement of a film thickness of a thin film formed on the sample substrate 11, in the grazing incidence X-ray fluorescence spectrometer 1.

The glancing angle α is set to the desired glancing angle α of 0.05°, and the sample S is sequentially measured. For example, 50 μl of a sample that is solution is dripped and dried on the sample substrate 11 by using a micropipette, and the sample substrate 11 is placed as the sample S on a sample table (not shown) of the grazing incidence X-ray fluorescence spectrometer 1, and the measurement of an element in the sample S is started.

In the grazing incidence X-ray fluorescence spectrometer 1 according to the first embodiment of the present invention, the slit member 6 is moved by the slit member moving unit 7 having a simple structure to set the glancing angle α of the X-ray beam 5 to a desired angle. Thus, the glancing angle α is set to an optimal glancing angle, by using a low-cost simple structure, in various measurement such as quantitative determination of the element that is dripped and dried on the sample substrate 11, and measurement of the film thickness of the thin film formed on the sample substrate 11, thereby performing analysis with high sensitivity and high accuracy.

A grazing incidence X-ray fluorescence spectrometer 30 according to a second embodiment of the present invention will be described with reference to FIG. 3. The grazing incidence X-ray fluorescence spectrometer 30 according to the second embodiment of the present invention is different from the grazing incidence X-ray fluorescence spectrometer 1 according to the first embodiment of the present invention in the slit member and the bent spectroscopic device. The grazing incidence X-ray fluorescence spectrometer 30 includes a filter 34 and an applied-voltage variable unit 32 which are not included in the grazing incidence X-ray fluorescence spectrometer 1 according to the first embodiment of the present invention. The different components will be descried.

A slit member of the grazing incidence X-ray fluorescence spectrometer 30 according to the second embodiment of the present invention is a variable slit member 36 in which the width of the linear opening 61 is variable. The width of the linear opening 61 of the variable slit member 36 may be continuously varied or may be varied stepwise. An initial width of the linear opening 61 is set to a minimal width.

Figure 4:
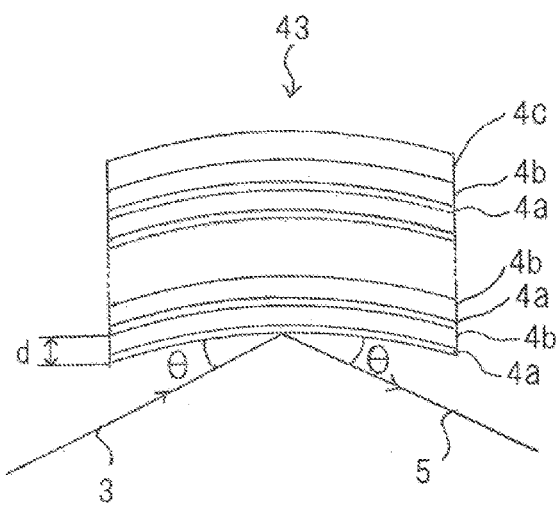
FIG. 4 is a schematic diagram illustrating a bent spectroscopic device of the spectrometer.
Figure 6:
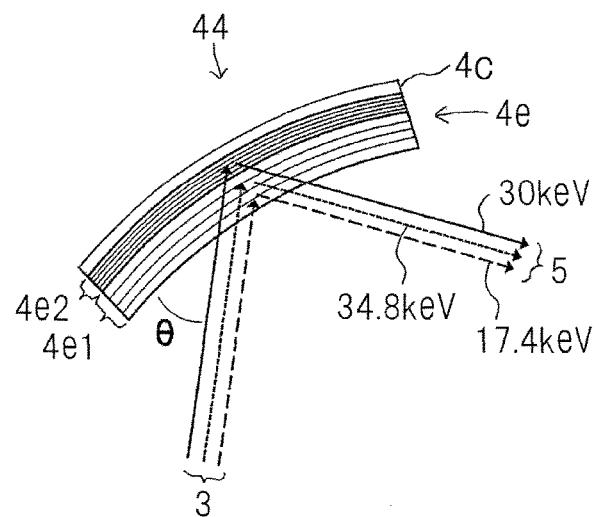
FIG. 6 is a schematic diagram illustrating a bent spectroscopic device, of the spectrometer, different from that shown in FIG. 4.

A bent spectroscopic device 43 of the grazing incidence X-ray fluorescence spectrometer 30 according to the second embodiment of the present invention is formed as a multi-layer film in which a plurality of layer pairs each formed from a reflective layer 4a and a spacer layer 4b and each having a predetermined cycle length d, are layered on a substrate 4c, and a ratio of a thickness of the reflective layer 4a to a thickness of the spacer layer 4b is 1:1.4 to 1:4, as shown in FIG. 4. Alternatively, as shown in FIG. 6, a bent spectroscopic device 44 is formed as a plurality of multi-layer films 4e in each of which a plurality of layer pairs each formed from the reflective layer 4a and the spacer layer 4b and each having a predetermined cycle length d are layered on the substrate 4c, and the closer the multilayer film 4e is to the substrate 4c, the less the predetermined cycle length d is. The cycle length represents a d value of a thickness of one set, that is, one layer pair of the reflective layer 4a and the spacer layer 4b layered over each other.

Figure 5:
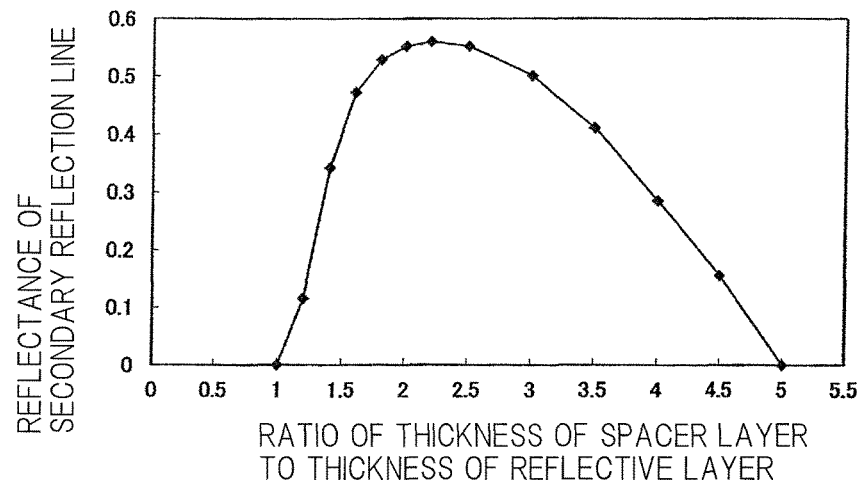
FIG. 5 illustrates a relationship between: a ratio of a thickness of a reflective layer to a thickness of a space layer; and reflectance of a secondary reflection line.

Specifically, as shown in FIG. 4, the bent spectroscopic device 43 is formed as the multilayer film in which the plurality of layer pairs each having: the reflective layer 4a; and the spacer layer 4b that includes an element of an atomic number that is smaller than an atomic number of an element of the reflective layer 4a, are layered on the substrate 4c such that the reflective layer 4a and the spacer layer 4b alternate with each other. In consideration of the actual thickness of each layer 4a, 4b being greater than or equal to 8 Å, a ratio of the thickness of the reflective layer 4a to the thickness of the spacer layer 4b is preferably 1:1.4 to 1:4, and more preferably 1:1.8 to 1:3, in order to strongly reflect a secondary reflection line. FIG. 5 shows reflectance of the secondary reflection line plotted against a ratio of the thickness of the spacer layer 4b to the thickness of the reflective layer 4a. For example, in this case, it is assumed that a ratio of the thickness of the reflective layer 4a to the thickness of the spacer layer 4b is 1:2 and the d value is 40.7 Å. When the bent spectroscopic device 43 is disposed such that the incident angle θ is 0.5°, the Mo-Kα line of 17.4 keV that forms the characteristic X-rays emitted from the X-ray source 2 having the molybdenum target are strongly reflected as a primary reflection line, and, simultaneously, continuous X-rays of 34.8 keV are strongly reflected as the secondary reflection line.

In the grazing incidence X-ray fluorescence spectrometer 30 having the bent spectroscopic device 43, in addition to the effect of the first embodiment of the present invention being obtained, not only the characteristic X-rays emitted from the X-ray source 2 but also the continuous X-rays having ½ of a wavelength of the characteristic X-rays, are strongly reflected to simultaneously irradiate the sample S therewith. Therefore, analysis can be accurately performed fast over a wide range of wavelength without providing of a plurality of X-ray sources and an X-ray source selection unit that selects one X-ray source from among the plurality of X-ray sources.

Specifically, as shown in FIG. 6, in the bent spectroscopic device 44, for example, the number of stages of the multi-layer films is two. A multilayer film 4e2 is formed by 20 layer pairs each having the reflective layer 4a and the spacer layer 4b being layered on the substrate 4c such that a ratio of the thickness of the reflective layer 4a to the thickness of the spacer layer 4b is 1:1, and the predetermined cycle length d value is 23.7Å. Continuous X-rays of 30 keV are strongly reflected by the multilayer film 4e2. A multilayer film 4e1 is formed by 20 layer pairs each having the reflective layer 4a and the spacer layer 4b being layered on the substrate 4c through the multilayer film 4e2 such that a ratio of the thickness of the reflective layer 4a to the thickness of the spacer layer 4b is 1:1, and the predetermined cycle length d value is 40.7Å. The Mo-Kα line of 17.4 keV which forms the characteristic X-rays emitted from the X-ray source 2 having the molybdenum target, are strongly reflected by the multilayer film 4e1. The bent spectroscopic device 44 is disposed such that the incident angle θ is 0.5°. The number of the stages of the multilayer films may be greater than or equal to 3. The multilayer films are set such the closer the multilayer film is to the substrate 4c, the less the predetermined cycle length d is. Therefore, as X-rays have lower energy and are more easily absorbed, the X-rays are reflected at a shallow position closer to the incident surface, and an efficiency of the reflection is high as a whole.

In the bent spectroscopic device 44, similarly to the bent spectroscopic device 43, the multilayer film 4e1 is more preferably formed such that a ratio of the thickness of the reflective layer 4a to the thickness of the spacer layer 4b is, for example, 1:2, so as to allow the multilayer film 4e1 to strongly reflect the secondary reflection line of 34.8 keV as well as the primary reflection line of the Mo-Kα line of 17.4 keV while the multilayer film 4e2 is allowed to strongly reflect the continuous X-rays of 30 keV.

The bent spectroscopic device 43, 44 is disposed such that, for example, the incident angle θ of the X-rays 3 is 0.5° at the center portion. As the position on which the X-rays 3 are incident is distant from the center portion, the incident angle θ continuously varies. According thereto, the predetermined cycle length d of the multilayer film is continuously changed, whereby focusing characteristics and monochromaticity for the X-ray beam 5 can be improved.

The grazing incidence X-ray fluorescence spectrometer 30 according to the second embodiment of the present invention has: the filter 34 that is movable forward into and backward from an X-ray optical path from the X-ray source 2 to the sample S, and that has a higher transmittance on the high energy side (short wavelength side); and/or the applied-voltage variable unit 32 that can vary a voltage applied to the X-ray source 2. The filter 34 and/or the applied-voltage variable unit 32 allow an intensity ratio among a plurality of X-rays that are included in the X-ray beam 5 and have different energies to be changed.

The filter 34 is formed as a plate member that is formed from, for example, Al, Cu, or Zr, has a thickness suitable for a purpose of the analysis, and has a higher transmittance on the high energy side in the X-ray optical path from the X-ray source 2 to the sample S. The filter 34 may be disposed between the slit member 36 and the sample S as shown in FIG. 3, between the X-ray source 2 and the bent spectroscopic device 43, 44, or between the bent spectroscopic device 43, 44 and the slit member 36 so as to be movable forward and backward. The filter 34 can be moved forward and backward by a forward/backward movement allowing unit 35.

Figure 7:
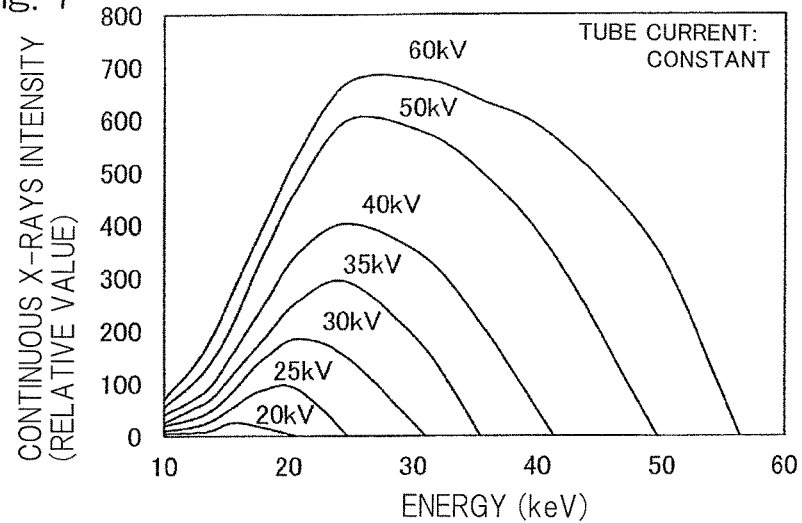
FIG. 7 illustrates a relationship between voltage applied to an X-ray source and distribution of intensity of continuous X-rays.

As shown in FIG. 7, the higher the voltage applied to the X-ray source 2 by the applied-voltage variable unit 32 is, the more intensely the continuous X-rays are generated on the high energy side. Therefore, the applied-voltage variable unit 32 allows the intensity ratio among the plurality of X-rays that are included in the X-ray beam 5 and have different energies to be changed, thereby optimally analyzing an element to be measured can be done.

Next, an operation of the grazing incidence X-ray fluorescence spectrometer 30, according to the second embodiment of the present invention, which includes the bent spectroscopic device 44 that strongly reflects, for example, the Mo-Kα line of 17.4 keV, and the continuous X-rays of 30 keV and 34.8 keV, will be described. In an operation similar to the operation of the grazing incidence X-ray fluorescence spectrometer 1 according to the first embodiment of the present invention, the glancing angle setting unit 8 sets the glancing angle α to 0.05°. At this time, the width of the linear opening 61 of the variable slit member 36 is set to the minimal width that is the initial width.

Figure 8:
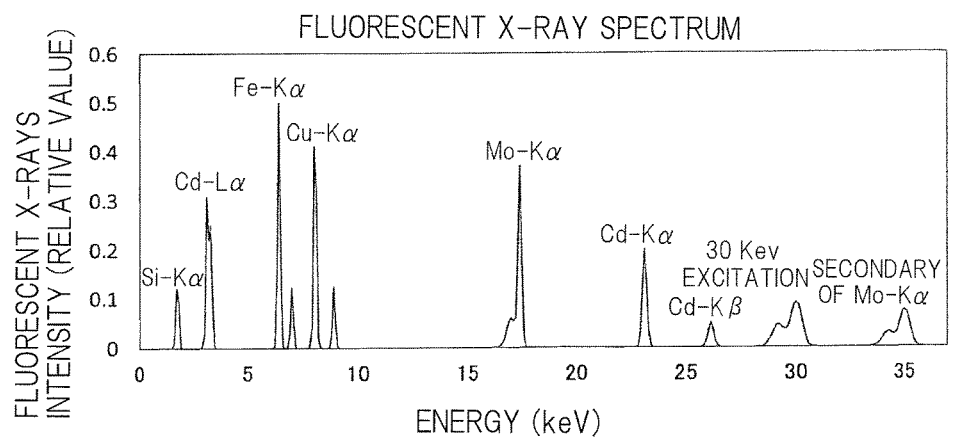
FIG. 8 illustrates a fluorescent X-ray spectrum measured by the grazing incidence X-ray fluorescence spectrometer according to the second embodiment of the present invention.

The glancing angle α is set to 0.05°, and the sample S obtained by, for example, a sample of a solution containing cadmium, iron, and copper being dripped and dried on the sample substrate 11, is placed on a sample table (not shown), and measured. FIG. 8 shows the fluorescent X-ray spectrum of the measured sample S.

By the bent spectroscopic device 44 of the grazing incidence X-ray fluorescence spectrometer 30, as shown in FIG. 6, the continuous X-rays of 34.8 keV (the secondary reflection line of the Mo-Kα line) and 30 keV, in addition to the characteristic X-rays of 17.4 keV (Mo-Kα line) emitted from the X-ray source 2 having the molybdenum target, are strongly reflected as excitation X-rays, and the sample S is irradiated with the excitation X-rays. A Fe-Kα line of 6.4 keV and a Cu-Kα line of 8.0 keV are intensely generated from the sample S by excitation at 17.4 keV, and a Cd-Kα line of 23.1 keV is intensely generated from the sample S by excitation at 34.8 keV and 30 keV, and iron, copper, and cadmium can be measured with high sensitivity. Excitation can be caused in cadmium by either of 34.8 keV or 30 keV.

In the grazing incidence X-ray fluorescence spectrometer 30 having the bent spectroscopic device 44, in addition to the effect of the first embodiment of the present invention being obtained, X-rays having different energies are reflected by the plurality of multilayer films having the cycle lengths d different from each other in the depth direction, and the cycle length d is set such that the closer the multilayer film is to the substrate 4c, the less the cycle length d is. Therefore, as X-rays have lower energy and are more easily absorbed, the X-rays are reflected at a shallow position closer to the incident surface, and the efficiency of the reflection is high as a whole, and analysis can be accurately performed fast over a wide range of wavelength without providing of a plurality of X-ray sources and an X-ray source selection unit that selects one X-ray source from among the plurality of X-ray sources.

Next, an operation of the grazing incidence X-ray fluorescence spectrometer 30, according to the second embodiment of the present invention, which includes the bent spectroscopic device 44 and includes the filter 34 that is inserted between the slit member 36 and the sample S (as indicated by an alternate long and two short dashes line in FIG. 3) after the glancing angle α is set, will be described. In an operation similar to the operation of the grazing incidence X-ray fluorescence spectrometer 1 according to the first embodiment of the present invention, the glancing angle setting unit 8 sets the glancing angle α to 0.05°. At this time, the width of the linear opening 61 of the variable slit member 36 is set to the minimal width that is the initial width.

Figure 3:
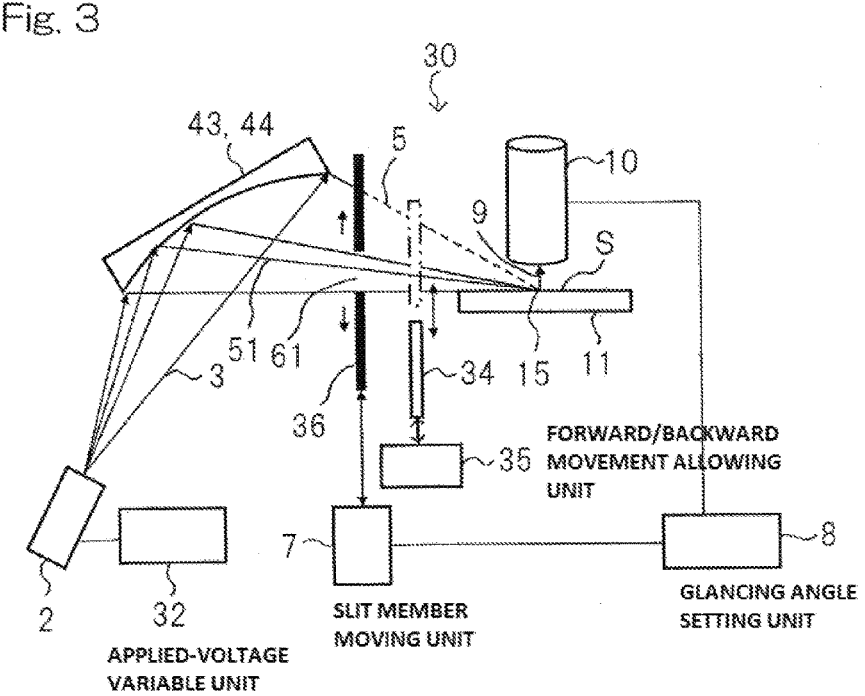
FIG. 3 is a schematic diagram illustrating a grazing incidence X-ray fluorescence spectrometer according to a second embodiment of the present invention.
Figure 9:
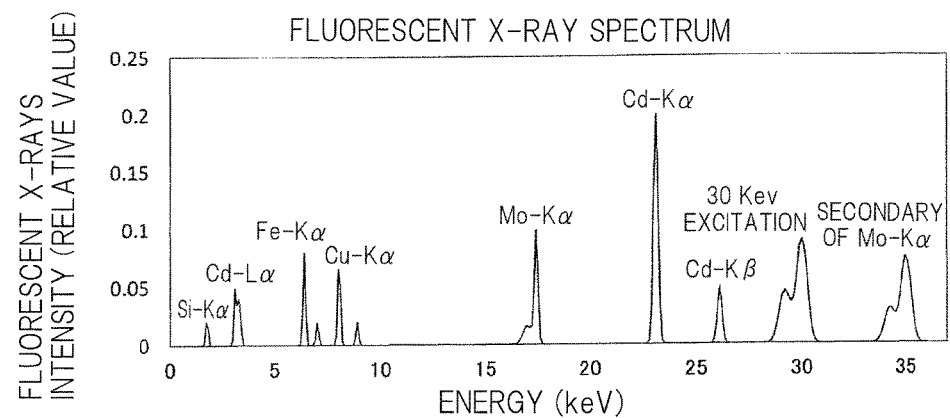
FIG. 9 illustrates a fluorescent X-ray spectrum measured by a filter being inserted in an X-ray optical path in the spectrometer.

The glancing angle α is set to 0.05°, and the filter 34 that is, for example, an aluminium plate having the thickness of 2 mm is inserted between the slit member 36 and the sample S by the forward/backward movement allowing unit 35 as shown in FIG. 3, to measure the sample S. FIG. 9 shows the fluorescent X-ray spectrum of the measured sample S. As can be seen from FIG. 9, as compared to the fluorescent X-ray spectrum shown in FIG. 8, the intensity of the Mo-Kα line is reduced, and the intensities of the X-rays which are lower than or equal to 17.4 keV of the Mo-Kα line in energy and which are caused by excitation by the Mo-Kα line, are reduced while change of the intensities at 30 keV and 34.8 keV (the secondary reflection line of the Mo-Kα line) are small. Thus, the intensity ratio among the plurality of X-rays that are included in the X-ray beam 5 and that have different energies, can be changed.

In the grazing incidence X-ray fluorescence spectrometer 30 that includes the bent spectroscopic device 44 and includes the filter 34 which has a higher transmittance on a high energy side in the X-ray optical path from the X-ray source 2 to the sample S, and which is inserted after the glancing angle α is set, in addition to the effect of the first embodiment of the present invention being obtained, reductions of the intensities of the X-rays on the high energy side are not great, and the intensities of the X-rays on the low energy side are reduced, whereby influence of an interfering line on the low energy side can be reduced. In particular, in a case where analyzing of an element on the high energy side is performed, signals of the fluorescent X-rays other than those of the element to be analyzed are eliminated, and a so-called dead time of the detector 10 can be shortened.

Next, an operation of the grazing incidence X-ray fluorescence spectrometer 30, according to the second embodiment of the present invention, which includes the bent spectroscopic device 44 and the filter 34, and in which the width of the linear opening 61 of the variable slit member 36 is made wider than the initial width after the glancing angle α is set, will be described. In an operation similar to the operation of the grazing incidence X-ray fluorescence spectrometer 30, according to the second embodiment of the present invention, which includes the bent spectroscopic device 44 and the filter 34, the glancing angle setting unit 8 sets the glancing angle α to 0.05°. At this time, the width of the linear opening 61 of the variable slit member 36 is set to the minimal width that is the initial width. In a case where, when the glancing angle α is set, the width of the linear opening 61 of the variable slit member 36 is set to be wider than the initial width, the focusing angle ø of the X-ray beam 5 is increased, and the gradient of change of the intensity of the Si-Kα line in the relationship, shown in FIG. 2, between the glancing angle α and the intensity of the fluorescent X-rays 9 becomes gentle, and accuracy for calculating the glancing angle α by the glancing angle setting unit 8 is reduced. Therefore, when the glancing angle α is set, the width of the linear opening 61 of the variable slit member 36 is set to the minimal width. For example, the minimal width of the linear opening 61 of the variable slit member 36 is set such that the focusing angle is 0.01°, and a maximal width thereof is set such that the focusing angle is 1°.

Figure 10:
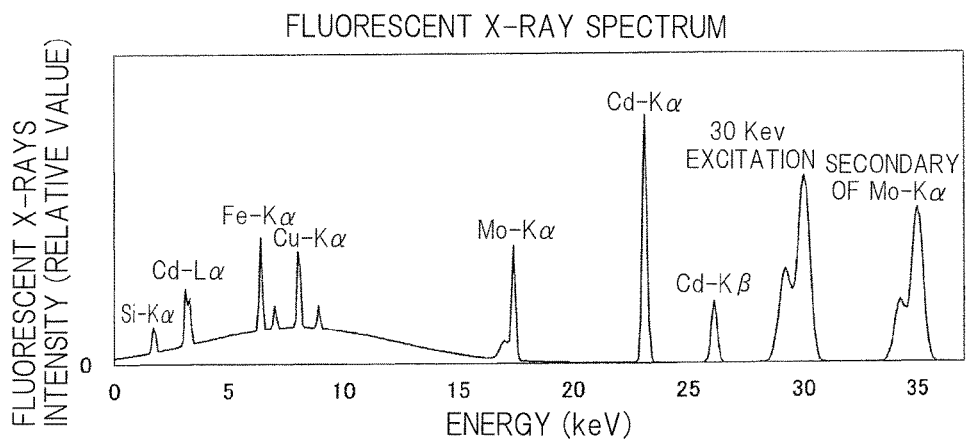
FIG. 10 illustrates a fluorescent X-ray spectrum measured by a linear opening of a variable slit member of the spectrometer being widened.

When the glancing angle α has been set to 0.05°, the width of the linear opening 61 of the variable slit member 36 is set to be greater than the initial width so as not to irradiate the end surface of the sample substrate 11 with the X-ray beam 5, and the sample S is measured. FIG. 10 shows the fluorescent X-ray spectrum of the sample S measured when the linear opening 61 is set to be wide and the filter 34 is inserted. The width of the linear opening 61 of the variable slit member 36 is set to be wide, whereby the sample S is irradiated with the X-ray beam 5 having a higher intensity, and, as can be seen from FIG. 10, the sample S is irradiated with the X-rays of 34.8 keV (the secondary reflection line of the Mo-Kα line) and 30 keV as excitation X-rays with a higher intensity as compared to that in the fluorescent X-ray spectrum shown in FIG. 9, and the Cd-Kα line of 23.1 keV is more intensely generated to measure cadmium with enhanced sensitivity.

As shown in FIG. 10, in a case where the linear opening 61 of the variable slit member 36 is widened and the sample S is irradiated with the X-ray beam 5 as the primary X-rays, the focusing angle of the X-ray beam 5 is increased, and X-rays that are included in the X-ray beam 5 and are incident on the sample S at an angle greater than the critical angle, enter the sample substrate 11 to increase the background of the continuous X-rays. Most of the continuous X-rays that are background, have energy lower than 20 keV, and do not appear in an energy region, of 20 keV or higher, where the Cd-Kα line (23.1 keV) can be observed. Therefore, in a case where the fluorescent X-rays 9 of 20 keV or higher is to be measured, the width of the linear opening 61 of the variable slit member 36 is widened, the sample S is irradiated with the X-ray beam 5 having a higher intensity, and the fluorescent X-rays 9 to be measured are intensely generated and can be measured with high sensitivity.

In the grazing incidence X-ray fluorescence spectrometer 30 which includes the bent spectroscopic device 44 and in which the width of the linear opening 61 of the variable slit member 36 is set to be wider than the initial width after the glancing angle α is set, in addition to the effect of the first embodiment of the present invention being obtained, the width of the X-ray beam 5 that passes through the slit member 6 can be made variable to change the focusing angle ø according to the purpose of the analysis, thereby performing measurement with enhanced sensitivity and accuracy.

As shown in FIG. 7, the higher a voltage applied to the X-ray source 2 is, the more intensely the continuous X-rays are generated on the high energy side (short wavelength side). Therefore, when the applied-voltage variable unit 32 allows the intensity ratio among the plurality of X-rays that are included in the X-ray beam 5 and have different energies to be changed, an element to be measured can be optimally analyzed. When the same voltage is applied, energy distribution of continuous X-rays intensity does not change, and the X-rays intensity changes in proportion to a tube current. The upper limit (maximum ratings) is defined for electric power (applied voltage×tube current) that can be applied to the X-ray source, and setting needs to be performed below the upper limit. In the operation of the grazing incidence X-ray fluorescence spectrometer 30 according to the second embodiment of the present invention as described above, in a case where an element to be measured is an element such as cadmium for which an excitation line on the high energy side is used, the applied voltage is preferably 60 kV. In a case where an element to be measured is iron or copper, the applied voltage is preferably reduced to 50 kV to increase tube current.

Advantages in another example of the analysis according to the present invention will be described below. In analysis for measuring the particle diameters of nanoparticles on the substrate, and for determining distribution of the nanoparticles on the substrate, the grazing incidence X-ray fluorescence spectrometer 1 or the grazing incidence X-ray fluorescence spectrometer 30 is used to sequentially irradiate the sample S with a plurality of X-rays that are included in the X-ray beam 5 and have different energies, change the glancing angle α, and measure the fluorescent X-rays 9 generated from the sample S, whereby accuracy for measuring the particle diameters of the nanoparticles is enhanced, and accuracy for determining whether the nanoparticles are distributed on the surface of the substrate or a part of the nanoparticles have entered the substrate can be enhanced.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS 1, 30 . . . grazing incidence X-ray fluorescence spectrometer
2 . . . X-ray source
3 . . . X-rays
4 . . . bent spectroscopic device
5 . . . X-ray beam
6, 36 . . . slit member
7 . . . slit member moving unit
8 . . . glancing angle setting unit
9 . . . fluorescent X-rays
10 . . . detector
15 . . . fixed position on surface of sample
61 . . . linear opening
S . . . sample
α . . . glancing angle

What is claimed is:

1. A grazing incidence X-ray fluorescence spectrometer comprising:
an X-ray source configured to emit X-rays;
a bent spectroscopic device configured to monochromate the X-rays emitted from the X-ray source and form an X-ray beam that is focused on a fixed position on a surface of a sample;
a movable slit member disposed between the bent spectroscopic device and the sample, the movable slit member having a linear opening by which a width of the X-ray beam is limited in a focusing angle direction; and
a detector configured to measure an intensity of fluorescent X-rays generated from the sample that is irradiated with the X-ray beam,
wherein the movable slit member sets a glancing angle of the X-ray beam based on the intensity of the fluorescent X-rays measured by the detector.

2. The grazing incidence X-ray fluorescence spectrometer as claimed in claim 1, wherein the movable slit member comprises a variable slit member that allows a width of the linear opening to be variable.

3. The grazing incidence X-ray fluorescence spectrometer as claimed in claim 1, wherein:
the bent spectroscopic device comprises one of:
a multilayer film including a substrate and a plurality of layer pairs, each layer pair including a reflective layer and a spacer layer, and each layer pair having a predetermined cycle length are layered on the substrate, of the multilayer film, such that a ratio of a thickness of the reflective layer to a thickness of the spacer layer is 1:1.4 to 1:4; and a plurality of multilayer films and a substrate, in each multilayer film of which a plurality of layer pairs, each layer pair including a reflective layer and a spacer layer, and each layer pair having a predetermined cycle length, are layered on the substrate, the plurality of multilayer films being formed such that the closer the multilayer film is to the substrate, the less the predetermined cycle length is.

4. The grazing incidence X-ray fluorescence spectrometer as claimed in claim 3, further comprising:

a filter configured to be movable forward into and backward from an X-ray optical path from the X-ray source to the sample, the filter having a higher transmittance on a high energy side, wherein an intensity ratio among a plurality of X-rays that are included in the X-ray beam and that have different energies is changed by the filter.

5. The grazing incidence X-ray fluorescence spectrometer of claim 1, wherein the movable slit member increases the glancing angle by moving upward relative to the surface of the sample.

6. The grazing incidence X-ray fluorescence spectrometer of claim 1, wherein the movable slit member sets the glancing angle to an angle that is less than a critical angle.

7. A method, comprising:

emitting, by an X-ray source of a spectrometer, X-rays;

forming, by a bent spectroscopic device of the spectrometer that is configured to monochromate the X-rays emitted from the X-ray source, an X-ray beam that is focused on a fixed position on a surface of a sample;

measuring, by a detector of the spectrometer, an intensity of fluorescent X-rays generated from the sample that is irradiated with the X-ray beam; and setting, by a movable slit member of the spectrometer that is disposed between the bent spectroscopic device and the sample, a glancing angle of the X-ray beam based on the intensity of the fluorescent X-rays measured by the detector, wherein the movable slit member includes a linear opening by which a width of the X-ray beam is limited in a focusing angle direction.

* * * * *